United States Patent
Danscher

(10) Patent No.: US 11,730,858 B2
(45) Date of Patent: Aug. 22, 2023

(54) GOLD PARTICLES FOR USE IN THERAPY TO PREVENT OR REDUCE CAPSULAR CONTRACTURE

(71) Applicant: Safe Implant Technology ApS, Charlottenlund (DK)

(72) Inventor: Gorm Danscher, Aarhus (DK)

(73) Assignee: Safe Implant Technology ApS, Charlottenlund (DK)

( * ) Notice: Subject to any disclaimer, the term of this patent is extended or adjusted under 35 U.S.C. 154(b) by 0 days.

(21) Appl. No.: 16/605,445

(22) PCT Filed: Apr. 13, 2018

(86) PCT No.: PCT/EP2018/059527
§ 371 (c)(1),
(2) Date: Oct. 15, 2019

(87) PCT Pub. No.: WO2018/192852
PCT Pub. Date: Oct. 25, 2018

(65) Prior Publication Data
US 2020/0046879 A1     Feb. 13, 2020

(30) Foreign Application Priority Data

Apr. 21, 2017  (EP) ..................... 17167655

(51) Int. Cl.
*A61L 27/04* (2006.01)
*A61L 27/30* (2006.01)

(52) U.S. Cl.
CPC ........... *A61L 27/306* (2013.01); *A61L 27/047* (2013.01); *A61L 2300/102* (2013.01)

(58) Field of Classification Search
None
See application file for complete search history.

(56) References Cited

U.S. PATENT DOCUMENTS

| | | | | |
|---|---|---|---|---|
| 2006/0121079 A1* | 6/2006 | Danscher | ............... | A61P 29/00 424/422 |
| 2009/0254179 A1 | 10/2009 | Burnett | | |
| 2010/0234945 A1* | 9/2010 | O'Leary | ............... | A61L 27/18 623/8 |
| 2014/0194852 A1* | 7/2014 | Danscher | ............... | A61K 33/24 604/506 |

FOREIGN PATENT DOCUMENTS

| WO | 2006/007489 | 1/2006 |
|---|---|---|
| WO | 2007/095582 | 8/2007 |

OTHER PUBLICATIONS

International Search Report dated Jul. 16, 2018 in PCT/EP2018/059527.
Heron et al.: "A technique for accessory cervical heart transplantation in rabbits and rats", Acta Pathol. Microbiol. Scand., [A] 1971; 79(4):366-372].
Lim et al.: "Accessory heart graft as a surgical model in studies of transplantation immunology", Ann Acad. Med., Singapore 1991; 20(4):478-483].
Stoltenberg et al.: "In vitro liberation of charged gold atoms. Autometallographic tracing of gold ions released by macrophages grown on metallic gold surfaces", Histochem Cell Biol., 128, 1-6, 2007.
Ferre: "New insight into the regulation of liver inflammation and oxidative stress", Mini Rev. Med. Chem. 6, 1321-1330, 2006.
Zhe Li, Moyuan Cao, Peng Li, Yuyan Zhao, Haoyu Bai, Yuchen Wu, Lei Jiang, "Surface-Embedding of Functional Micro-/Nanoparticles for Achieving Versatile Superhydrophobic Interfaces, Matter" vol. 1, Issue 3, 2019, pp. 661-673.
Jang et al., "Measurements of T1- and T2-relaxation Time Changes According to the Morphological Characteristics of Gold Nanoparticles (GNPs)," J. Korean Soc. Reason. Med., 15, pp. 48-56 (2011).

* cited by examiner

*Primary Examiner* — Danah Al-Awadi
(74) *Attorney, Agent, or Firm* — Fox Rothschild LLP; Carol E. Thorstad-Forsyth

(57) ABSTRACT

Gold implant having a cross-section in the range of 20-100, preferably in the range of 20-40 μm for use in therapy to prevent or reduce capsular contracture. Further, the invention relates to a method of producing a gold-coated implant.

6 Claims, 2 Drawing Sheets a          b          c

GOLD PARTICLES FOR USE IN THERAPY TO PREVENT OR REDUCE CAPSULAR CONTRACTURE

CROSS-REFERENCE TO RELATED APPLICATIONS

The present application is the U.S. National Phase Entry of International Patent Application No. PCT/EP2018/059527 filed on Apr. 13, 2018 and entitled "GOLD PARTICLES FOR USE IN THERAPY TO PREVENT OR REDUCE CAPSULAR CONTRACTURE," which claims priority to European Patent Application No. 17167655.4 filed on Apr. 21, 2017, the contents of which are incorporated herein by reference in their entireties.

INTRODUCTION

The invention relates to metallic gold, and gold embedded into or coated onto the surface of implants as well as uses thereof. Further, the invention relates to a method for producing a gold-coated implant.

BACKGROUND ART

After implantation of a silicone implant into the human or animal body, a fibrous capsule i.e. scarring tissue forms around the implant shell. Capsular contracture is a condition mainly known from patients with silicone implants such as breast implant but may occur with similar implants in other body parts as well. The occurrence of capsular formation seems to follow from the formation of tightly-woven collagen fibers, resulting from the immune system response to foreign objects surgically installed into the human body, e.g. breast implants, artificial pacemakers, orthopedic prostheses and dental implants.

Capsular contracture itself is believed to occur when the collagen-fiber capsule shrinks, tightens and compresses the implant. It is a medical complication that can be painful and discomforting and might distort the aesthetics of the implant and the affected body part. For example, the breast may be hard and painful to the touch, and appears abnormal.

Capsular contracture is a multi-factual fibrotic process, the precise cause of which is unknown. Although the cause of capsular contracture is unknown, factors common to its incidence include bacterial contamination, rupture of the breast-implant shell, leakage of the silicone-gel filling, and hematoma.

Moreover, capsular contracture may be a consequence of the immune system defending the patient's bodily integrity and health, and it might reoccur, even after the requisite corrective surgery for the initial incidence.

The surgical implantation methods that have reduced capsular contracture include submuscular breast implant placement, using either textured or polyurethane-coated implants, limited handling of the implants, minimal contact with the chest wall skin before their insertions, and irrigation of the surgical sites with triple-antibiotic solutions. The correction of capsular contracture might require surgical removal of the capsule and breast implant. Closed capsulotomy (disrupting the capsule via external manipulation), a once-common maneuver for treating hard capsules, was discontinued because it might rupture the breast implant. Most recently, autologous fat transfer has been tried.

Non-surgical methods of treating capsules include massage, external ultrasound, treatment with leukotriene pathway inhibitors (e.g. Accolate, Singulair), and pulsed electromagnetic field therapy.

The methods to prevent or reduce capsular contracture described above are usually marginally effective, painful, expensive, and often the capsular contracture reoccur following the procedure of removal. Hence, there remains a need for finding safe solutions to prevent or reducing formation of capsular contracture following a surgical insertion of augmentation implants.

On this background it is an object of the present invention to provide a safe alternative which is easy to apply and superior to the known approaches for preventing or reducing capsular contracture.

SUMMARY OF THE INVENTION

This and further objects are in a first aspect of the present invention achieved by providing gold particles having a cross-section in the range of 20-100 μm, preferably in the range of 20-40 μm and having a purity of greater than 99.00% w/w, preferably 99.99% w/w for use in therapy or prophylactic therapy in the prevention or reduction of capsular contracture. According to the present invention, the gold particles can when implanted in a human, serve as a means for diminishing and maintaining a low local immune response, thereby reducing the amount of granulation tissue formed and decreasing the risk of the host developing capsular contracture in the proximity of a gold implant. Upon implantation of gold particles in the proximity of an implant such as a silicone implant, local macrophages will attach themselves to the metallic gold. The inflammatory cells produce an ultra-thin layer, a dissolution membrane, on the metallic surface within which the macrophages may control the chemical milieu at the surface of the gold implant to facilitate dissolucytosis of gold ions. The dissolution membrane is a 10-100 nm thick bio-layer membrane essential for the dissolution of surface of the gold particles. The dissolucytosis within the dissolution membrane is most likely caused by the capability of the macrophages to release cyanide ions and alter the oxygen tension and the pH in their vicinity (Larsen A, Stoltenberg M. & Danscher, G (2007) *In vitro liberation of charged gold atoms. Autometallographic tracing of gold ions released by macrophages grown on metallic gold surfaces* 128, 1-6 Histochem Cell Biol.; Ferre N, Claria, J (2006) *New insight into the regulation of liver inflammation and oxidative stress.* Mini Rev. Med. Chem. 6, 1321-1330.). The inflammatory cells i. e. macrophages release cyanide into the dissolution membrane and into their immediate surroundings, and the following chemical process occurs:

$$4Au + 8CN^- + 2H_2O + O_2 = 4[Au(CN)_2]^- + 4OH^-$$

The complex ion aurocyanide $Au(CN)_2^-$, which is a relatively stable ion, inhibits the lysosomal enzymes of inflammatory cells in the synovial tissue and decreases the number of inflammatory cells in situ. It was surprisingly found by the inventor that the gold implants having the effect of reducing the local immune response also contributes in preventing or reducing the amount of granulation tissue.

The cross-section of the gold implant should be larger than 20 μm, as such cross-section ensures that the implant will have the necessary dimension in order not to be phagocytosed by macrophages or other immune cells of the immune system of the host. If the gold implant is too large the surface area available for biorelease of gold ions will decrease drastically. Also, using larger gold implants is not cost efficient. In this aspect it is preferred to design a gold implant with a large surface area such as a flake or having a spherical appearance. The gold implant may take any shape when used in therapy to prevent or reduce capsular contracture such as a spherical particle, bead, flake, rod, cube, polygon, thread, such as a gold thread micron ball or spiral and the implants may be solid or hollow. It is to be understood that the cross section being in the range of 20-100 μm allows for the cross-section to be any size as long as it is at least 20 μm and not larger than 100 μm. A gold particle size above 100 μm is not cost efficient and larger sized gold particles may be too heavy to easily disperse in a coating solution or other means for administering and hence it will not be possible to deliver the implant correctly. Any size of a cross-section above 20 μm of the gold particle will have the desired effect of reducing inflammation.

In a preferred embodiment the cross-section of the gold implant is in the range of 20-40 microns. An implant of such a size is preferred in some cases, since the small size allows for easier distribution, and larger surface area by weight compared to larger particles. Also, by keeping the implants small, the price per implant is lower since the amount of gold is lower.

Gold suitable for use in the present invention is pure gold having a purity greater than 99.00% w/w, most preferred the gold is of a purity greater than about 99.99% w/w. Side-effects, caused by the high systemic exposure to gold ions that results from treatment with gold salts, has dramatically reduced the use of gold drugs in the western world over the last decades.

New research, now has shown that gold ions liberated from metallic gold by macrophages do not spread further away than about 500 microns from the locality where the gold is implanted. Thus gold enriched prosthesis implants will cause exposure to gold ions only in tissue in direct contact with the prosthesis implant is thus more safe to use.

The gold implant or the gold particles according to embodiments of the present invention may be implanted or positioned in the host in a number of different ways, e.g. during a procedure, one or more gold implants or gold implants according to the present invention may be implanted or positioned in the proximity of the implant.

In an embodiment of the present invention, the gold particle is to be implanted in the proximity of an implant. Such implants may be silicone implants, both liquid and solid, saline implants, or composite implants, preferably implants that are used are selected from abreast, hip, buttocks, triceps and/or biceps, pectoral, calf, chest, chin, forearm, shoulder or abdominal implant. In a preferred embodiment, the implant is a silicon implant.

In another aspect of the invention, the gold particles according to the invention are embedded in the wall of the implant in such a way that the gold particles are part of the surface of the implant. The metallic gold surfaces may be distributed across the surface with an average distance of approximately 200 microns, i.e. the surface may be dotted with gold particles embedded in the outermost layer of the capsule.

The gold particles are applied to the surface of the implant e.g. by adding a thin layer of gold particle containing material (e.g. gold dispersed in the same material as that of the implant). In that way a considerable amount of the gold particles will be part of the outer surface of the implant. A foam structure of the outmost layer of the implant, for example made of polyurethane, might increase the amount of gold particles that are in direct contact with host tissue due to the increased surface-area to size-of-implant.

The thin layer of gold particles is applied and/or adhered to the implant surface by dipping or submerging the implant into a physiological acceptable solution e.g. comprising hyaluronic acid and at least 0.1 g/L of gold particles according to the invention, which corresponds to approximately 7,200,000 gold particles. Preferably the concentration of gold particles is 5 g/L gold. The gold particles are of a purity above 99.00% w/w, preferably 99.99% w/w and are sized from 20 to 100 microns. The 0.1 g/L concentration of gold particles results in approximately 36 gold particles per cubic millimetre of coating solution. After dipping in the coating solution comprising gold particles according to the invention, the gold coated implant is thus retrieved from the solution and allowed to dry. The gold-coated implant may be placed in sterile wrapping until use or directly implanted into the human body.

In a method of preventing capsular contracture, it may be possible to increase the amount of gold ions released from the gold particles in situ by increasing the temperature of the gold particles of the implant by inductive coupling of a radio-frequency magnetic field prior to or after implantation. The inductive heating of the gold in an oscillating magnetic field is a non-invasive way of establishing an increase of temperature in the gold particles. Thus, the gold particle or gold coated implant according to the invention may immediately prior to or after implanting the gold-coated implant in a human body be heated by electromagnetic waves having frequencies in the range of 3 to 300 GHz to a temperature above 37° C. and below 42° C., preferably to a temperature of 39° C.

The increased temperature of the gold particles will increase macrophage activity after implantation and thereby cause an increased release of gold ions from the gold particles.

In one embodiment, the heating may be done by using magnetic resonance imaging (MRI). When using MRI it is possible to visualize the temperature distribution in biological tissues in a non-invasive way. By mapping temperature sensitive chemical shifts, it is known to the skilled person how to create a picture of the relative temperature distribution. In this way, it is possible to decide the optimal frequencies for obtaining a temperature shift to 39° C. or any other desired temperature above 37° C. and below 42° C.

BRIEF DESCRIPTION OF THE DRAWINGS

The drawings described in the following are to support the detailed description. The invention will be described with reference to the drawings in which.

DETAILED DESCRIPTION OF THE INVENTION

Figure 1:
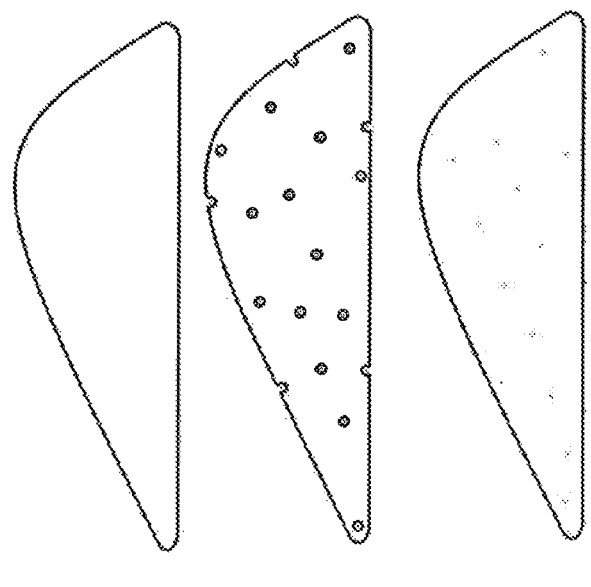
FIG. 1 is a schematic drawing of an implant comprising gold particles either embedded in or onto the surface of the implant (a) and (b), respectively, or coated onto the surface (c) of the implant.
Figure 2:
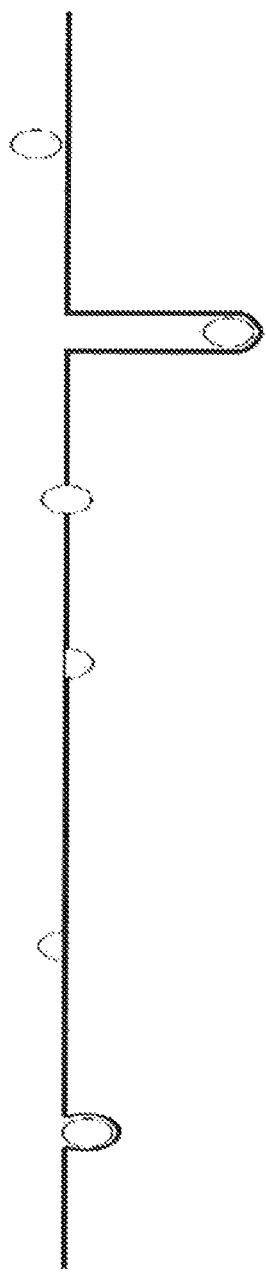
FIG. 2 is an enlarged view of implant (b) comprising gold particles embedded in the surface of the implant.

When used herein, the term gold or gold particle is to be understood as metallic pure gold i.e. having a gold content of greater than 99.00% w/w, preferably 99.99% w/w, not a solute such as gold ions in a medium or a gold alloy. By introducing gold particles according to the present invention in proximity, onto or into the surface of an implant such as a silicon implant, the dissolucytosis of the gold i.e. release of gold ions into the local tissue will suppress the local immune response, thereby suppressing capsular contracture around the implant in the host. The inhibition/prevention of capsular contracture may be due to the local decrease in amount of granulation tissue and to the immune suppressing effect obtained by the biorelease of the gold ions. Due to the necessity of dissolucytosis in order for the anti-capsular contracture properties of metallic gold to be effective, gold particles must be placed in proximity of/next to or embedded in the implant or introduced in directly on the surface. For example, the implant may be powdered with sterile gold particles just before placing the implant in the body. The implant must be administered in a way enabling accessibility of macrophages to exert dissolucytical release of gold ions into the immediate surroundings of the prosthesis i.e. in the implant tissue zone.

In one embodiment of the invention the gold particles are embedded into the surface of the implant whereby they constitute part of the implant surface. The gold particles may be distributed randomly within the surface of the implant or in a certain pattern. The distance between the gold particles should not exceed 500 microns.

The gold particles may be applied to the tissue surrounding the implant prior to insertion of the implant. One dose treatment is sufficient since the gold will remain for a lifetime in the tissue of the patient where it has been placed. The gold particles may also be provided with the implant, i.e. when embedded in the surface of the implant or adhered to the surface of the implant.

Once the device is implanted in the body the gold particles will slowly be released upon exposure to the aqueous environment but will stay put in a narrow zone around the implant thereby creating a gold aura around the implant.

Because of the presence of metallic gold with a large surface area, gold ions will be released in a more powerful manner into the implant-tissue zone suppressing the amount of granulation tissue around the implant and inhibit any inflammation that might arise in the implant-tissue zone for an long period of time i.e. most likely for as long as the person lives.

The following describes experimental research supporting the effect of the invention.

EXAMPLES

Experiments were performed on ten animals using the Animal model "Heterotopic heart transplantation to the neck vessels in rats". The animal model was originally described in 1971 by Heron et al. [Heron I., A technique for accessory cervical heart transplantation in rabbits and rats, Acta Pathol. Microbiol. Scand., [A] 1971; 79(4):366-372] and later a few modifications were added by Lim et al. [Lim S M, Li S Q., Accessory heart graft as a surgical model in studies of transplantation immunology, Ann Acad. Med., Singapore 1991; 20(4):478-483]. It is a well-established surgical model for in vivo studies of transplantation immunology and has been widely used the last 20 years.

In accordance with the invention 100 mg of gold particles as disclosed herein having a surface area that is greater than that of a solid sphere having a weight comparable to a gold particle and at least one cross-section between 40-250 µm were used per operation. The gold particles were poured onto the transplanted heart just before the wound was closed. The animals lived 5 to 6 days before the transplanted heart stopped. When analyzing cross-sections from the transplanted heart surrounded by granulose tissue, it was found that almost all cells on the skin close part of the heart were loaded with released gold ions while on the opposite side of the heart the granulose tissue was completely void of gold accumulations in the cells. It was also observed that the gold treated granulose tissue was distinctly growth inhibited. This was found to be true for all ten animals undergoing transplantation.

The invention claimed is:

1. A medical device, comprising:
    a gold coated implant comprising gold particles (i) that are at least partially embedded in an outermost layer of the gold coated implant and (ii) from which gold ions are released into a tissue around the gold coated implant when disposed in a host,
    wherein the gold coated implant is at least partially formed of silicone, saline, foam, polyurethane, or a composite material,
    wherein the gold particles have a cross-section in the range of 20-100 µm, have a purity greater than 99.00% w/w, and are distributed across a surface of the gold coated implant with an average distance of 200 microns, and
    wherein a distance between adjacent ones of the gold particles does not exceed 500 microns.

2. The medical device according to claim 1, wherein each of the gold particles is solid or hollow and shaped as a spherical particle, bead, flake, rod, cube, polygon, thread, spiral or gold thread micron ball.

3. The medical device according to claim 1, wherein said gold coated implant comprises a breast implant, a hip implant, a buttocks implant, a triceps implant and/or a biceps implant, a pectorial implant, a chin implant, a calf implant, a chest implant, a forearm implant, a shoulder implant, or an abdominal implant.

4. The medical device according to claim 3, wherein the implant is a silicone implant.

5. The medical device according to claim 1, wherein an effective amount of the gold particles is administered into the tissue surrounding the implant accessible for contact with immune cells of the individual.

6. The medical device according to claim 1, further comprising a source of electromagnetic waves emitted in a direction towards the gold particles immediately prior to or after the gold coated implant is positioned inside the host to increase a temperature of each said gold particle to a temperature above 37° C. and below 42° C.

* * * * *